United States Patent
Hilpert et al.

(10) Patent No.: US 9,044,426 B2
(45) Date of Patent: Jun. 2, 2015

(54) ANTIMICROBIAL PEPTIDES FOR TREATMENT OF INFECTIOUS DISEASES

(71) Applicant: Dorian Bevec, Germering (DE)

(72) Inventors: Kai Hilpert, Weingarten (DE); Ralf Mikut, Karlsruhe (DE); Serge Ruden, Pforzheim (DE)

(73) Assignee: Dr. Roland Berecz, Debrecen (HN)

( * ) Notice: Subject to any disclaimer, the term of this patent is extended or adjusted under 35 U.S.C. 154(b) by 0 days.

(21) Appl. No.: 14/350,598

(22) PCT Filed: Oct. 10, 2012

(86) PCT No.: PCT/EP2012/070079
§ 371 (c)(1),
(2) Date: Apr. 9, 2014

(87) PCT Pub. No.: WO2013/053772
PCT Pub. Date: Apr. 18, 2013

(65) Prior Publication Data
US 2014/0235531 A1 Aug. 21, 2014

Related U.S. Application Data

(60) Provisional application No. 61/629,790, filed on Nov. 28, 2011.

(30) Foreign Application Priority Data

Oct. 10, 2011 (EP) ..................... 11008188

(51) Int. Cl.
*A01N 37/18* (2006.01)
*A61K 38/04* (2006.01)
*A61K 38/00* (2006.01)
*A61P 31/10* (2006.01)
*A61K 38/08* (2006.01)
*C07K 7/06* (2006.01)

(52) U.S. Cl.
CPC .. *A61K 38/08* (2013.01); *C07K 7/06* (2013.01)

(58) Field of Classification Search
CPC ................... A61K 38/08; C07K 7/06
See application file for complete search history.

(56) References Cited

FOREIGN PATENT DOCUMENTS

| KR | 20110083551 A | 7/2011 |
| WO | 2006-050611 A1 | 5/2006 |
| WO | 2008-022444 A1 | 2/2008 |
| WO | 2009-117524 A2 | 9/2009 |

OTHER PUBLICATIONS

Curry et al. Opportunistic protozoan infections in human immunodeficiency virus disease: Review highlighting diagnostic and therapeutic aspects. J Clin Pathol. 1991, vol. 44, pp. 182-193.*
D. Mania et al: "Screening for Antifungal Peptides and Their Modes of Action in *Aspergillus nidulans*", Applied and Environmental Microbiology, vol. 76, No. 21, Sep. 10, 2010, pp. 7102-7108, XP055020522.
Hilpert K et al: "High-throughput generation of small antibacterial peptides with improved activity", Nature Biotechnology, Nature Publishing Group, New York, NY, US, vol. 23, No. 8, Aug. 1, 2005, pp. 1008-1012, XP008096699. (Abstract).
Hilpert Kai et al: "Peptide arrays on cellulose support: SPOT synthesis, a time and cost efficient method for synthesis of large numbers of peptides in a parallel and addressable fashion", Nature Protocols 2007 LNKD PubMed:17545971, vol. 2, No. 6, 2007, pp. 1333-1349. (Abstract).
Partial European Search Report cited in EP 11 00 8188, dated Mar. 1, 2012, 10 pgs.
International Search Report cited in PCT/EP2012/070079, dated Dec. 6, 2012, 5 pgs.

* cited by examiner

*Primary Examiner* — Marcela M Cordero Garcia
(74) *Attorney, Agent, or Firm* — Rothwell, Figg, Ernst & Manbeck, P.C.

(57) ABSTRACT

The present invention is directed to the peptides WKWLKKWIK, WRKFWKYLK, and RRWRVIVKW and use of said peptides as therapeutic agents for the prophylaxis and/or treatment of infections, in particular bacterial and/or fungal infections and diseases caused by bacterial and/or fungal infections.

39 Claims, 2 Drawing Sheets

Fig. 1

| Sequence | | M. tuberculosis | M. smegmatis | P. aeruginosa | E. coli | S. typhi-murium | C. albicans | S. epidermidis | S. aureus | E. faecalis |
|---|---|---|---|---|---|---|---|---|---|---|
| WKWLKKWIK | (SEQ ID NO:1) | 1.1 | 1.9 | 2.9 | 5.8 | 11.5 | 5.8 | 0.7-0.35 | 0.7 | 11.5 |
| WRKFWKYLK | (SEQ ID NO:2) | 3.0 | 1.5 | 6.0 | 0.8 | 6.0 | 3.0 | 0.8 | 0.8 | 6.0 |
| RLWWWWRRK | (SEQ ID NO:4) | 4.1 | 2.4 | 16.6 | 4.1 | 8.3 | 4.1 | 0.5 | 2.1 | 4.1 |
| KWKWWWRKI | (SEQ ID NO:5) | 4.2 | 6.4 | 4.6 | 4.6 | 4.6 | 4.6 | 1.2 | 1.2 | 4.6 |
| RIRRWKFRW | (SEQ ID NO:6) | 4.3 | 1.4 | 42.6 | 5.3 | 5.3 | 21.3 | 1.3 | 1.3 | 5.3 |
| RLKRWWKFL | (SEQ ID NO:7) | 4.5 | 3.0 | 9.8 | 1.2 | 4.9 | 9.8 | 1.2 | 2.4 | 9.8 |
| RRWWRWWVW | (SEQ ID NO:8) | 5.6 | 11.4 | 2.6 | 0.7 | 2.6 | 10.4 | 0.7 | 1.3 | 2.6 |
| WFKMRWWGR | (SEQ ID NO:9) | 5.9 | 2.2 | 46.1 | 5.8 | 23.1 | 11.5 | 2.9 | 2.9 | 11.5 |
| KFKWWRMLI | (SEQ ID NO:10) | 6.1 | 15.3 | 4.6 | 0.6 | 2.3 | 4.6 | 0.6 | 1.2 | 2.3 |
| RWRWWWRVY | (SEQ ID NO:11) | 8.0 | 6.7 | 13.2 | 1.6 | 3.3 | 13.2 | 1.6 | 3.3 | 3.3 |
| LKRRWKWWI | (SEQ ID NO:12) | 8.8 | 5.1 | 19.1 | 2.4 | 9.6 | 19.1 | 1.2 | 2.4 | 9.6 |
| RRRIKIRWY | (SEQ ID NO:13) | 8.9 | 1.5 | 38.2 | 0.6 | 9.5 | 19.1 | 1.2 | 2.4 | 9.5 |
| RLWWKIWLK | (SEQ ID NO:14) | 9.0 | 3.8 | 22.5 | 2.8 | 11.3 | 5.6 | 1.4 | 1.4 | 5.6 |
| KRRWRIWLV | (SEQ ID NO:15) | 9.1 | 2.7 | 3.0 | 3.0 | 3.0 | 12.0 | 1.5-0.75 | 1.5 | 3.0 |
| FFIYVWRRR | (SEQ ID NO:16) | 11.9 | 1.3 | 15.3 | 3.8 | 7.6 | 7.6 | 1.0 | 1.9 | 3.8 |
| IRMIRIVLL | (SEQ ID NO:17) | 13.7 | 0.3 | 16.0 | 2.0 | 4.0 | 16.0 | 2.0 | 4.0 | 16.0 |
| RWWRKIWKW | (SEQ ID NO:18) | 16.6 | 8.3 | 2.2 | 8.8 | 8.8 | 4.4 | 1.1 | 2.2 | 4.4 |
| RWWIRIRWH | (SEQ ID NO:19) | 17.0 | 1.6 | 10.7 | 1.3 | 2.7 | 10.7 | 1.3 | 1.3 | 2.7 |
| RRRWWKLMM | (SEQ ID NO:20) | 17.6 | 2.2 | 11.0 | 2.7 | 11.0 | 21.9 | 2.7-1.4 | 5.5 | 21.9 |
| LRRWIRIRW | (SEQ ID NO:21) | 17.7 | 2.2 | 21.4 | 0.7 | 5.4 | 10.7 | 1.3-0.65 | 1.3 | 5.4 |
| RKFRWWVIR | (SEQ ID NO:22) | 17.8 | 3.7 | 21.9 | 2.7.0 | 5.5 | 21.9 | 1.4-0.52 | 1.4 | 10.9 |
| WKIVFWWRR | (SEQ ID NO:23) | 23.3 | 4.4 | 21.9 | 1.4 | 2.7 | 5.5 | 0.7 | 1.4 | 2.7 |
| RQRRVVIWW | (SEQ ID NO:24) | 24.7 | 1.9 | 10.7 | 1.3 | 5.3 | 21.4 | 1.3 | 2.7 | 5.3 |
| RRWRVIVKW | (SEQ ID NO:3) | 24.7 | 2.3 | 2.7 | 1.3 | 2.7 | 5.4 | 0.7 | 1.3 | 2.7 |

Fig. 1 continued

| Sequence | M. tuberculosis | M. smegmatis | P. aeruginosa | E. coli | S. typhi-murium | C. albicans | S. epidermidis | S. aureus | E. faecalis |
|---|---|---|---|---|---|---|---|---|---|
| RKWKIKWYW (SEQ ID NO.:25) | 34.5 | 2.9 | 5.2 | 0.7 | 2.6 | 10.5 | 1.3 | 2.6 | 5.2 |
| YRLRVKWKW (SEQ ID NO.:26) | 36.0 | 1.5 | 14.3 | 3.6 | 7.1 | 3.6 | 0.9 | 1.8 | 7.1 |
| WKWRVRVTI (SEQ ID NO.:27) | 51.5 | 0.8 | 5.4 | 1.3 | 2.7 | 10.8 | 1.3 | 2.7 | 2.7 |
| RTKKWIVWI (SEQ ID NO.:28) | 78.1 | 9.8 | 11.6 | 1.4 | 5.8 | 23.1 | 2.9 | 5.8 | 11.6 |
| KRKKRFKWW (SEQ ID NO.:29) | 141.0 | 8.8 | 165-80.3 | 20.6 | 20.6 | 41.2 | 2.6 | 2.6 | 10.3 |

SEQUENCE LISTING

```
<160> NUMBER OF SEQ ID NOS: 29

<210> SEQ ID NO 1
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO: 1
<222> LOCATION: (1)..(9)

<400> SEQUENCE: 1

Trp Lys Trp Leu Lys Lys Trp Ile Lys
1               5

<210> SEQ ID NO 2
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:2
<222> LOCATION: (1)..(9)

<400> SEQUENCE: 2

Trp Arg Lys Phe Trp Lys Tyr Leu Lys
1               5

<210> SEQ ID NO 3
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:3
<222> LOCATION: (1)..(9)

<400> SEQUENCE: 3

Arg Arg Trp Arg Val Ile Val Lys Trp
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:4
<222> LOCATION: (1)..(9)

<400> SEQUENCE: 4

Arg Leu Trp Trp Trp Trp Arg Arg Lys
1               5

<210> SEQ ID NO 5
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:5
<222> LOCATION: (1)..(9)

<400> SEQUENCE: 5

Lys Trp Lys Trp Trp Trp Arg Lys Ile
1               5

<210> SEQ ID NO 6
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:6
<222> LOCATION: (1)..(9)

<400> SEQUENCE: 6

Arg Ile Arg Arg Trp Lys Phe Arg Trp
1               5

<210> SEQ ID NO 7
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:7
<222> LOCATION: (1)..(9)

<400> SEQUENCE: 7

Arg Leu Lys Arg Trp Trp Lys Phe Leu
1               5

<210> SEQ ID NO 8
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:8
<222> LOCATION: (1)..(9)

<400> SEQUENCE: 8

Arg Arg Trp Trp Arg Trp Val Val Trp
```

```
1               5

<210> SEQ ID NO 9
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:9
<222> LOCATION: (1)..(9)

<400> SEQUENCE: 9

Trp Phe Lys Met Arg Trp Trp Gly Arg
1               5

<210> SEQ ID NO 10
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:10
<222> LOCATION: (1)..(9)

<400> SEQUENCE: 10

Lys Phe Lys Trp Trp Arg Met Leu Ile
1               5

<210> SEQ ID NO 11
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:11
<222> LOCATION: (1)..(9)

<400> SEQUENCE: 11

Arg Trp Arg Trp Trp Trp Arg Val Tyr
1               5

<210> SEQ ID NO 12
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:12
<222> LOCATION: (1)..(9)

<400> SEQUENCE: 12

Leu Lys Arg Arg Trp Lys Trp Trp Ile
1               5

<210> SEQ ID NO 13
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:13
<222> LOCATION: (1)..(9)

<400> SEQUENCE: 13
```

```
Arg Arg Arg Ile Lys Ile Arg Trp Tyr
1               5
```

<210> SEQ ID NO 14
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:14
<222> LOCATION: (1)..(9)

<400> SEQUENCE: 14

```
Arg Leu Trp Trp Lys Ile Trp Leu Lys
1               5
```

<210> SEQ ID NO 15
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:15
<222> LOCATION: (1)..(9)

<400> SEQUENCE: 15

```
Lys Arg Arg Trp Arg Ile Trp Leu Val
1               5
```

<210> SEQ ID NO 16
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:16
<222> LOCATION: (1)..(9)

<400> SEQUENCE: 16

```
Phe Phe Ile Tyr Val Trp Arg Arg Arg
1               5
```

<210> SEQ ID NO 17
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:17
<222> LOCATION: (1)..(9)

<400> SEQUENCE: 17

```
Ile Arg Met Arg Ile Arg Val Leu Leu
1               5
```

<210> SEQ ID NO 18
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:18
<222> LOCATION: (1)..(9)

<400> SEQUENCE: 18

```
Arg Trp Trp Arg Lys Ile Trp Lys Trp
1               5

<210> SEQ ID NO 19
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:19
<222> LOCATION: (1)..(9)

<400> SEQUENCE: 19

Arg Trp Trp Ile Arg Ile Arg Trp His
1               5

<210> SEQ ID NO 20
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:20
<222> LOCATION: (1)..(9)

<400> SEQUENCE: 20

Arg Arg Arg Trp Trp Lys Leu Met Met
1               5

<210> SEQ ID NO 21
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:21
<222> LOCATION: (1)..(9)

<400> SEQUENCE: 21

Leu Arg Arg Trp Ile Arg Ile Arg Trp
1               5

<210> SEQ ID NO 22
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:22
<222> LOCATION: (1)..(9)

<400> SEQUENCE: 22

Arg Lys Phe Arg Trp Trp Val Ile Arg
1               5

<210> SEQ ID NO 23
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:23
<222> LOCATION: (1)..(9)
```

```
<400> SEQUENCE: 23

Trp Lys Ile Val Phe Trp Trp Arg Arg
1               5

<210> SEQ ID NO 24
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:24
<222> LOCATION: (1)..(9)

<400> SEQUENCE: 24

Arg Gln Arg Arg Val Val Ile Trp Trp
1               5

<210> SEQ ID NO 25
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:25
<222> LOCATION: (1)..(9)

<400> SEQUENCE: 25

Arg Lys Trp Lys Ile Lys Trp Tyr Trp
1               5

<210> SEQ ID NO 26
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:26
<222> LOCATION: (1)..(9)

<400> SEQUENCE: 26

Tyr Arg Leu Arg Val Lys Trp Lys Trp
1               5

<210> SEQ ID NO 27
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:27
<222> LOCATION: (1)..(9)

<400> SEQUENCE: 27

Trp Lys Trp Arg Val Arg Val Thr Ile
1               5

<210> SEQ ID NO 28
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:28
<222> LOCATION: (1)..(9)
```

```
<400> SEQUENCE: 28

Arg Thr Lys Lys Trp Ile Val Trp Ile
1               5

<210> SEQ ID NO 29
<211> LENGTH: 9
<212> TYPE: PRT
<213> ORGANISM: Artificial Sequence
<220> FEATURE:
<223> OTHER INFORMATION: nonapeptide
<220> FEATURE:
<221> NAME/KEY: SEQ ID NO:29
<222> LOCATION: (1)..(9)

<400> SEQUENCE: 29

Lys Arg Lys Lys Arg Phe Lys Trp Trp
1               5
```

ANTIMICROBIAL PEPTIDES FOR TREATMENT OF INFECTIOUS DISEASES

CROSS REFERENCE TO RELATED APPLICATION

This application is a 35 U.S.C. 371 National Phase Entry Application from PCT/EP2012/70079, filed Oct. 10, 2012, which claims the benefit of European Patent Application No. 11008188.2 filed on Oct. 10, 2011 and U.S. Provisional Application No. 61/629,790 filed Nov. 28, 2011, the disclosures of which are incorporated herein in their entirety by reference.

The present invention is directed to the combination of antimicrobial peptides WKWLKKWIK (SEQ ID NO.:1), WRKFWKYLK (SEQ ID NO.:2), and RRWRVIVKW (SEQ ID NO.:3), and use of said peptides as therapeutic agents for the prevention and/or treatment of infections, e.g. bacterial infections and diseases caused by bacterial infections.

BACKGROUND OF THE INVENTION

The immune system in higher vertebrates represents the first line of defense against various antigens that can enter the vertebrate body, including microorganisms such as bacteria, fungi and viruses that are the causative agents of a variety of diseases.

There is a medical need for new therapies for the prevention and treatment of bacterial infections, especially bacterial infections caused by Gram-negative bacteria, and multiple drug-resistant bacteria. Currently, bacterial infections are treated with various antibiotics. Although antibiotics are effective in the treatment of various bacterial infections, there are a number of limitations to the effectiveness and safety of antibiotics. For example, some individuals have an allergic reaction to certain antibiotics and other individuals suffer from serious side effects. Moreover, continued misuse of antibiotics for the treatment of bacterial infections contributes to formation of antibiotic-resistant strains of bacteria.

Antimicrobial peptides (AMPs) are an important part of innate immunity in the fight against pathogens. AMPs not only kill bacteria, but also fungi, parasites, enveloped viruses and cancer cells. Antimicrobial peptides (AMPs) can be found in virtual all forms of life; more than 1500 naturally occurring peptides have been discovered and their sequences are accessible in different databases, for example "*The Antimicrobial Peptide database*" (http://aps.unmc.edu/AP/main-.php). Cationic AMPs consist of 12 to 80 amino acids, have a positive net charge, exhibit some degree of amphiphilicity, and have a range of different structures, such as alpha-helical, beta sheets and loops. Sequence analysis of natural AMPs has identified 146 different clusters, which demonstrates the diversity inherent in this group. Over decades of research, it has become increasingly clear that AMPs not only kill Gram-positive and Gram-negative bacteria, but also fungi, enveloped viruses such as HIV, and parasites like *Plasmodium falciparum*, the main cause for malaria in humans. New antibiotics with a novel mechanism of action are particularly difficult to find, even with the massive screening and sequencing approaches from the pharmaceutical industry. Especially short AMPs are ideal medicinal drug candidates for economical reasons.

Thus, an object of the present invention is to provide compositions comprising newly developed synthetic peptides WKWLKKWIK (SEQ ID NO.:1), WRKFWKYLK (SEQ ID NO.:2), and RRWRVIVKW (SEQ ID NO.:3), alone or in combination, and use of said peptides in combination or as single therapeutic agents for the prophylaxis and/or treatment of infections, in particular bacterial infections and diseases caused by bacterial infections.

The teaching of the independent claims solves this object of the present invention. Further advantageous features, aspects and details of the invention are evident from the dependent claims, the description, and the examples of the present application.

BRIEF DESCRIPTION OF THE DRAWINGS

FIG. 1: Table showing antimicrobial activity of selected peptides.

DESCRIPTION OF THE INVENTION

According to the present invention, novel nonapeptides (i.e. peptides consisting of nine amino acids) were synthesized. It was found that these nonapeptides show antimicrobial activity against a broad range of microorganisms, including bacteria, fungi, enveloped viruses and protozoans.

Thus, a first aspect of the invention relates to a composition comprising a combination of the nonapeptides having the sequences

```
                                          (SEQ ID NO.: 1)
Trp-Lys-Trp-Leu-Lys-Lys-Trp-Ile-Lys  (WKWLKKWIK);

(SEQ ID NO.: 2)
Trp-Arg-Lys-Phe-Trp-Lys-Tyr-Leu-Lys  (WRKFWKYLK);

(SEQ ID NO.: 3)
Arg-Arg-Trp-Arg-Val-Ile-Val-Lys-Trp  (RRWRVIVKW).
```

A further aspect of the invention relates to a composition comprising the nonapeptide having the sequence

```
                                          (SEQ ID NO.: 1)
Trp-Lys-Trp-Leu-Lys-Lys-Trp-Ile-Lys  (WKWLKKWIK).
```

Still a further aspect of the invention relates to a composition comprising the nonapeptide having the sequence

```
                                          (SEQ ID NO.: 2)
Trp-Arg-Lys-Phe-Trp-Lys-Tyr-Leu-Lys  (WRKFWKYLK).
```

Still a further aspect of the invention relates to a composition comprising the nonapeptide having the sequence

```
                                          (SEQ ID NO.:3)
Arg-Arg-Trp-Arg-Val-Ile-Val-Lys-Trp  (RRWRVIVKW).
```

These peptides show strong activity against tested pathogens, demonstrating a broad range activity as anti-infectives.

Thus, in a preferred embodiment, the compositions according to the invention are for use in medicine, e.g. human or veterinary medicine.

In a further preferred embodiment, a composition according to the invention, i.e. a composition comprising the nonapeptide of SEQ ID NO.:1, a composition comprising the nonapeptide of SEQ ID NO.:2, a composition comprising the nonapeptide of SEQ ID NO.:3, or a composition comprising a combination of the nonapeptides of SEQ ID NOs.:1-3, is for use in the prevention and/or treatment of infections. Preferably, the composition is for use in the prevention and/or treatment of infections with microorganisms or diseases caused by microorganisms. Specifically, the present invention relates to the peptides WKWLKKWIK (SEQ ID NO.:1), WRKFWKYLK (SEQ ID NO.:2), and/or RRWRVIVKW (SEQ ID NO.:3) for use in the prophylaxis and/or treatment of infections caused by bacteria, fungi, viruses and/or parasites, and diseases caused by the respective infections. The prophylaxis and/or treatment of e.g. Gram-negative, Gram-positive bacterial infections, mycobacterial infections, fungal infections, and diseases caused by those pathogens.

In the context of the present invention, the term "microorganism" refers to a microscopic or submicroscopic organism, including viruses, bacteria, fungi, and protozoans.

In a particularly preferred embodiment of the invention, the composition comprising a combination of the nonapeptides of SEQ ID NOs.:1-3, the composition comprising the nonapeptide of SEQ ID NO.:1, the composition comprising the nonapeptide of SEQ ID NO.:2, or the composition comprising the nonapeptide of SEQ ID NO.:3, is for use in the prevention and/or treatment of bacterial infections or diseases caused by bacteria.

The bacteria responsible for the infection or disease are preferably Gram-negative bacteria, Gram-positive bacteria or bacteria of the genus *Mycobacterium*.

Especially preferred Gram-negative bacteria in the context of the present invention are those of the genus *Pseudomonas, Escherichia* and *Salmonella*, in particular *Pseudomonas aeruginosa, Escherichia coli*, and *Salmonella typhimurium*.

Especially preferred Gram-positive bacteria in the context of the present invention are those of the genus *Staphylococcus* and *Enterococcus*, in particular *Staphylococcus aureus, Staphylococcus epidermidis*, and/or *Enterococcus faecalis*.

Especially preferred *Mycobacteria* in the context of the present invention are *M. tuberculosis* and *M. smegmatis*, in particular *Mycobacterium tuberculosis*.

The fungi responsible for the infection or disease are preferably pathogenic yeast species, most preferably those of the genus *Candida*. Preferred *Candida* species are *C. glabrata* and *C. albicans*, in particular *Candida albicans*.

In a further particularly preferred embodiment of the invention, the composition comprising a combination of the nonapeptides of SEQ ID NOs.:1-3, the composition comprising the nonapeptide of SEQ ID NO.:1, the composition comprising the nonapeptide of SEQ ID NO.:2, or the composition comprising the nonapeptide of SEQ ID NO.:3, is for use in the prevention and/or treatment of protozoan infections or diseases caused by protozoans. Examples include *Entamoeba histolytica, Plasmodium* spec., *Giardia lamblia*, and *Trypanosoma brucei*. Especially preferred protozoans in the context of the present invention are those of the genus *Plasmodium*, in particular *Plasmodium falciparum*.

In further preferred embodiments, the bacteria have acquired resistance against at least one antibiotic or are multidrug-resistant bacteria.

In yet a further particularly preferred embodiment of the invention, the composition comprising a combination of the nonapeptides of SEQ ID NOs.:1-3, the composition comprising the nonapeptide of SEQ ID NO.:1, the composition comprising the nonapeptide of SEQ ID NO.:2, or the composition comprising the nonapeptide of SEQ ID NO.:3, is for use in the prevention and/or treatment of fungal infections or diseases caused by fungi.

In particular, the nonapeptides according to the invention show strong inhibitory effects against the following pathogens and diseases associated therewith.

*Pseudomonas aeruginosa* Infection

*Pseudomonas aeruginosa* is a Gram-negative, aerobic bacterium belonging to the family Pseudomonadaceae. It is a bacterium commonly found in soil and water. *Pseudomonas aeruginosa* has become increasingly recognized as an emerging opportunistic pathogen of clinical relevance. Several different epidemiological studies track its occurrence as a nosocomial pathogen and indicate that antibiotic resistance is increasing in clinical isolates.

*Pseudomonas aeruginosa* is an opportunistic pathogen, meaning that it exploits some break in the host defenses to initiate an infection. The bacterium almost never infects uncompromised tissues, yet there is hardly any tissue that it cannot infect if the tissue defenses are compromised in some manner. It causes urinary tract infections, respiratory system infections, dermatitis, soft tissue infections, bacteremia, bone and joint infections, gastrointestinal infections and a variety of systemic infections, particularly in patients with severe burns and in cancer and AIDS patients who are immunosuppressed. *Pseudomonas aeruginosa* infection is a serious problem in patients hospitalized with cancer, cystic fibrosis, and burns. The case fatality rate in these patients is near 50 percent.

Only a few antibiotics are effective against *Pseudomonas*, including fluoroquinolones, gentamicin and imipenem, and even these antibiotics are not effective against all strains. The futility of treating *Pseudomonas* infections with antibiotics is most dramatically illustrated in cystic fibrosis patients, virtually all of whom eventually become infected with a strain that is so resistant that it cannot be treated. Most *Pseudomonas* infections are both invasive and toxinogenic.

Diseases caused by *Pseudomonas aeruginosa* comprise endocarditis, respiratory infections, pneumonia, infections of cystic fibrosis patients, bacteremia, septicemia, central nervous system infections, ear infections including external otitis, eye infections, bone and joint infections, urinary tract infections, gastrointestinal infections, skin and soft tissue infections, including wound infections, pyoderma and dermatitis.

Within the hospital, *Pseudomonas aeruginosa* finds numerous reservoirs: disinfectants, respiratory equipment, food, sinks, taps, toilets, showers and mops. Furthermore, it is constantly reintroduced into the hospital environment on fruits, plants, vegetables, as well by visitors and patients transferred from other facilities. Spread occurs from patient to patient on the hands of hospital personnel, by direct patient contact with contaminated reservoirs, and by the ingestion of contaminated foods and water. *Pseudomonas aeruginosa* is frequently becoming multi drug-resistant to many commonly used antibiotics, and can also form biofilms on implanted medical devices.

The peptides of the invention show strong inhibitory effects on *Pseudomonas aeruginosa*. Thus, in a preferred embodiment the peptides WKWLKKWIK (SEQ ID NO.:1), WRKFWKYLK (SEQ ID NO.:2), and RRWRVIVKW (SEQ ID NO.:3) are especially useful for treatment and/or prophylaxis of *Pseudomonas aeruginosa* infection and diseases caused by *Pseudomonas aeruginosa* infection and *Pseudomonas aeruginosa* biofilms, as well as against *Pseudomonas aeruginosa* biofilm formation on medical implant devices.

*Escherichia coli* Infection

*Escherichia coli* (*E. coli*) is a Gram-negative bacterium. Certain strains of *E. coli* (e.g. enterotoxigenic *E. coli*, enteropathogenic *E. coli*, enteroinvasive *E. coli*, enterohemorrhagic *E. coli*, enteroaggregative *E. coli*, uropathogenic *E. coli*) can cause severe diarrhea, gastroenteritis, urinary tract infections, neonatal meningitis, haemolytic-uremic syndrome, peritonitis, mastitis, septicaemia, and Gram-negative pneumonia.

The peptides of the invention show strong inhibitory effects on *Escherichia coli*. Thus, in a preferred embodiment the peptides WKWLKKWIK (SEQ ID NO.:1), WRKF-WKYLK (SEQ ID NO.:2), and RRWRVIVKW (SEQ ID NO.:3) are especially useful for treatment and/or prophylaxis of *Escherichia coli* infection and diseases caused by *Escherichia coli* infection.

Salmonella Infection

*Salmonella* is a Gram-negative bacterium. Most people infected with *Salmonella* develop diarrhea, fever, vomiting, and abdominal cramps 12 to 72 hours after infection. In most cases, the illness lasts 4 to 7 days and most people recover without treatment. In severe cases, the *Salmonella* infection may spread from the intestines to the blood stream, and then to other body sites, and can cause death unless the person is treated promptly with antibiotics. The elderly, infants, and those with impaired immune systems are more likely to develop severe illness. Some people afflicted with salmonellosis later experience reactive arthritis, which can have long-lasting, disabling effects. A form of *Salmonella* named typhoidal *Salmonella* can lead to typhoid fever. Typhoid fever is a life-threatening illness.

The peptides of the invention show strong inhibitory effects on *Salmonella*. Thus, in a preferred embodiment the peptides WKWLKKWIK (SEQ ID NO.:1), WRKFWKYLK (SEQ ID NO.:2), and RRWRVIVKW (SEQ ID NO.:3) are especially useful for treatment and/or prophylaxis of *Salmonella* infection and diseases caused by *Salmonella* infection.

Staphylococcus aureus Infection

*Staphylococcus aureus* (*S. aureus*) is a Gram-positive coccal bacterium. *S. aureus* can cause a range of illnesses from skin infections, such as pimples, impetigo, boils, scalded skin syndrome, abscesses, to life-threatening diseases such as pneumonia, meningitis, osteomyelitis, endocarditis, toxic shock syndrome (TSS), bacteremia, sepsis, or cystic fibrosis. It is still one of the five most common causes of nosocomial infections, often causing postsurgical wound infections. *S. aureus* is extremely prevalent in atopic dermatitis patients who are less resistant to it than other people. It often causes complications, and this disease is mostly found in fertile, active places, including the armpits, hair, and scalp. A severe form, Ritter's disease, is seen in neonates. *S. aureus* is one of the causal agents of mastitis in dairy cows. Its large polysaccharide capsule protects the organism from recognition by the cow's immune defenses.

Methicillin-resistant *Staphylococcus aureus* (MRSA) is a type of bacteria that has evolved an ability to survive treatment with beta-lactam antibiotics, including penicillin, methicillin, oxacillin, amoxicillin and cephalosporins. MRSA is especially troublesome in hospital-associated infections. In hospitals, patients with open wounds, invasive devices, and weakened immune systems are at greater risk for infection than the general public.

The peptides of the invention show strong inhibitory effects on *Staphylococcus aureus*. Thus, in a preferred embodiment the peptides WKWLKKWIK (SEQ ID NO.:1), WRKFWKYLK (SEQ ID NO.:2), and RRWRVIVKW (SEQ ID NO.:3) are especially useful for treatment and/or prophylaxis of *Staphylococcus aureus* infection and diseases caused by *Staphylococcus aureus* infection.

Staphylococcus epidermidis Infection

*Staphylococcus epidermidis* is Gram-positive coccal bacterium arranged in grape-like clusters. It forms cohesive colonies that cause biofilms to grow on plastic devices placed within the body, most commonly on intravenous catheters and on medical prostheses. Another disease it causes is endocarditis. In patients with defective heart valves *Staphylococcus epidermidis* can cause endocarditis. Antibiotics are largely ineffective in clearing biofilms.

The peptides of the invention show strong inhibitory effects on *Staphylococcus epidermidis*. Thus, in a preferred embodiment the peptides WKWLKKWIK (SEQ ID NO.:1), WRKFWKYLK (SEQ ID NO.:2), and RRWRVIVKW (SEQ ID NO.:3) are especially useful for treatment and/or prophylaxis of *Staphylococcus epidermidis* infection and diseases caused by *Staphylococcus epidermidis* infection and biofilms on medical implant devices.

Enterococcus faecalis Infection

*Enterococcus faecalis* (*E. faecalis*) is a Gram-positive bacterium. *E. faecalis* can cause endocarditis, urinary tract infections (UTI), and meningitis. *E. faecalis* is associated with nosocomial infections including catheter-associated UTI, central line-associated bloodstream infection, and surgical site infections. *E. faecalis* is resistant to many commonly used antibiotics (aminoglycosides, aztreonam, cephalosporins, clindamycin, nafcillin, oxacillin, and trimethoprim-sulfamethoxazole). Resistance to vancomycin in *E. faecalis* is becoming more common.

The peptides of the invention show strong inhibitory effects on *Enterococcus faecalis*. Thus, in a preferred embodiment the peptides WKWLKKWIK (SEQ ID NO.:1), WRKFWKYLK (SEQ ID NO.:2), and RRWRVIVKW (SEQ ID NO.:3) are especially useful for treatment and/or prophylaxis of *Enterococcus faecalis* infection and diseases caused by *Enterococcus faecalis* infection.

Mycobacterium tuberculosis Infection

Tuberculosis (TB) is an often severe and contagious airborne disease caused by infection with *Mycobacterium tuberculosis*. TB typically affects the lungs but it also may affect any other organ of the body. It is usually treated with a regimen of drugs taken for six months to two years depending on the type of infection. TB infection begins when the mycobacteria reach the pulmonary alveoli, where they invade and replicate within alveolar macrophages. Bacteria are picked up by dendritic cells, which do not allow replication, although these cells can transport the bacilli to local lymph nodes. Further spread is through the bloodstream to the more distant tissues and organs where secondary TB lesions can develop in lung apices, peripheral lymph nodes, kidneys, brain, and bone.

Tuberculosis is classified as one of the granulomatous inflammatory conditions. Macrophages, T lymphocytes, B lymphocytes and fibroblasts are among the cells that aggregate to form a granuloma, with lymphocytes surrounding the infected macrophages. The granuloma functions not only to prevent dissemination of the mycobacteria, but also provides a local environment for communication of cells of the immune system. Within the granuloma, T lymphocytes (CD4+) secrete cytokines such as interferon gamma, which activates macrophages to destroy the bacteria with which they are infected. T lymphocytes (CD8+) can also directly kill infected cells. Importantly, bacteria are not always eliminated within the granuloma, but can become dormant, resulting in a latent infection. Another feature of the granulomas of human tuberculosis is the development of cell death, also called necrosis, in the center of tubercles. People with weakened immune systems (individuals with HIV disease, those receiving chemotherapy, or children under five years of age, for example) are at a greater risk for developing tuberculosis.

Multi drug-resistant Tuberculosis is a form of drug-resistant TB in which the TB bacteria can no longer be killed by at least the two best antibiotics, isoniazid and rifampin, commonly used to cure TB. As a result, this form of the disease is more difficult to treat than ordinary TB and requires up to two years of multidrug treatment. Extensively Drug-Resistant Tuberculosis is a less common form of multidrug-resistant TB in which the TB bacteria have changed enough to circumvent the two best antibiotics, isoniazid and rifampin, as well as most of the alternative drugs used against MDR TB. These second-line drugs include any fluoroquinolone, and at least one of the other three injectable anti-TB drugs: amikacin, kanamycin, or capreomycin. As a result, this form of the disease needs up to two years of extensive drug treatment and is the most challenging to treat.

The peptides of the invention show strong inhibitory effects on *Mycobacterium tuberculosis*. Thus, in a preferred embodiment the peptides WKWLKKWIK (SEQ ID NO.:1), and WRKFWKYLK (SEQ ID NO.:2) are especially useful for treatment and/or prophylaxis of *Mycobacterium tuberculosis* infection and diseases caused by *Mycobacterium tuberculosis* infection.

Examples for such diseases in addition to all forms of TB include but are not limited to Pott's disease and Poncet's disease. These diseases are mainly caused and/or promoted by a prior infection with *Mycobacterium tuberculosis.*

*Candida albicans* Infection

*Candida albicans* is a fungus causing candidiasis. Candidiasis is a term which comprises infections that are potentially life-threatening diseases in severely immunocompromised persons, such as cancer, transplant, and AIDS patients as well as non-trauma emergency surgery patients. *C. albicans* biofilms may form on the surface of implantable medical devices. Hospital-acquired infections in patients not previously considered at risk (e.g., patients in an intensive care unit) have become a cause of major health concern.

The peptides of the invention show strong inhibitory effects on *Candida albicans*. Thus, in a preferred embodiment the peptides WKWLKKWIK (SEQ ID NO.:1), WRKFWKYLK (SEQ ID NO.:2), and RRWRVIVKW (SEQ ID NO.:3) are especially useful for treatment and/or prophylaxis of *Candida albicans* infection and diseases caused by *Candida albicans* infection and biofilms on medical implant devices.

In a further embodiment the peptides WKWLKKWIK (SEQ ID NO.:1), WRKFWKYLK (SEQ ID NO.:2), and RRWRVIVKW (SEQ ID NO.:3) are used for the manufacture of a pharmaceutical composition. The pharmaceutical composition comprises a composition according to the invention as defined supra and thus may contain the nonapeptide of SEQ ID NO.:1, the nonapeptide of SEQ ID NO.:2, the nonapeptide of SEQ ID NO.:3, or a combination of the nonapeptides of SEQ ID NOs.:1-3.

In one embodiment, the pharmaceutical composition contains the nonapeptide of SEQ ID NO.:1 as the sole active ingredient. In a further embodiment, the pharmaceutical composition contains the nonapeptide of SEQ ID NO.:2 as the sole active ingredient. In yet a further embodiment, the pharmaceutical composition contains the nonapeptide of SEQ ID NO.:3 as the sole active ingredient. In yet a further embodiment, the pharmaceutical composition contains a combination of the nonapeptides of SEQ ID NOs.:1, 2, and 3 as the sole active ingredient.

Such pharmaceutical compositions comprise the peptides as active ingredients, together with at least one pharmaceutically acceptable carrier, excipient, binders, disintegrants, glidents, diluents, lubricants, coloring agents, sweetening agents, flavoring agents, preservatives or the like.

The pharmaceutical compositions of the present invention can be prepared in a conventional solid or liquid carrier or diluents and a conventional pharmaceutically made adjuvant at suitable dosage level in a known way. Preferably the peptides are suitable for intravenous administration or suitable for oral administration or suitable for administration by inhalation.

The pharmaceutical compositions of the present invention may be used for prophylaxis and/or treatment of bacterial infections and diseases caused by bacterial infections, wherein the pharmaceutical composition is for the preparation of a formulation for oral administration to newborns, toddlers, and/or infants.

In yet a further embodiment the peptide WKWLKKWIK (SEQ ID NO.:1) is used for the manufacture of a pharmaceutical composition for prophylaxis and/or treatment of bacterial infections and diseases caused by bacterial infections, wherein the pharmaceutical composition is for the preparation of a formulation for oral administration to newborns, toddlers, and/or infants.

In yet a further embodiment the peptide WRKFWKYLK (SEQ ID NO.:2), is used for the manufacture of a pharmaceutical composition for prophylaxis and/or treatment of bacterial infections and diseases caused by bacterial infections, wherein the pharmaceutical composition is for the preparation of a formulation for oral administration to newborns, toddlers, and/or infants.

In yet a further embodiment the peptide RRWRVIVKW (SEQ ID NO.:3) is used for the manufacture of a pharmaceutical composition for prophylaxis and/or treatment of bacterial infections and diseases caused by bacterial infections, wherein the pharmaceutical composition is for the preparation of a formulation for oral administration to newborns, toddlers, and/or infants.

The term "diseases caused by bacteria or fungi" refers to any disease, wherein the prior infection with bacteria or fungi is causative for the development of said disease. This applies also to diseases, wherein the infection with bacteria or fungi promotes the formation of said disease, without being the primary factor for said disease. Thus, a disease caused by bacteria or fungi refers specifically to diseases that occur preferably in infected subjects even though this disease might also occur in subjects without a prior bacteria or fungal infection, however, according to this invention said diseases occur with a greater probability in infected subjects, because of the prior bacteria or fungal infection. Consequently, treatment with the peptides is especially useful in diseases, wherein the infection with the bacteria or fungi aggrevates/promotes the development/occurence of said second or further disease.

In another embodiment the combination of peptides WKWLKKWIK (SEQ ID NO.:1), WRKFWKYLK (SEQ ID NO.:2), and RRWRVIVKW (SEQ ID NO.:3) is used for the manufacture of a pharmaceutical composition for prophylaxis and/or treatment of bacterial or fungal infections and diseases caused by bacterial or fungal infections, wherein the pharmaceutical composition is for the preparation of a lyophilized formulation or a buffered liquid formulation.

In yet another embodiment the combination of peptides WKWLKKWIK (SEQ ID NO.:1), WRKFWKYLK (SEQ ID NO.:2), and RRWRVIVKW (SEQ ID NO.:3) is used according to any one of the other embodiments for the manufacture of a pharmaceutical composition for prophylaxis and/or treatment of bacterial or fungal infections and diseases caused by bacterial or fungal infections, wherein the pharmaceutical composition is to be administered intravenously, orally, or by inhalation.

The combination of peptides WKWLKKWIK (SEQ ID NO.:1), WRKFWKYLK (SEQ ID NO.:2), and RRWRVIVKW (SEQ ID NO.:3) can be used as active ingredients, together with at least one pharmaceutically acceptable carrier, excipient and/or diluents for the manufacture of a pharmaceutical composition.

Administration forms include, for example, pills, tablets, film tablets, coated tablets, capsules, liposomal formulations, micro- and nano-formulations, powders and deposits. Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain the peptide.

The present invention also includes the mammalian milk as a formulation for oral administration of the peptide to newborns, toddlers, and infants, either as pharmaceutical preparations, and/or as dietary food supplements.

The peptides can also be administered in form of their respective pharmaceutically active salts. Suitable pharmaceutically active salts comprise acid addition salts and alkali or earth alkali salts. For instance, sodium, potassium, lithium, magnesium or calcium salts can be obtained.

The peptides also form pharmaceutically acceptable salts with organic and inorganic acids. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, D-o-tolyltartaric acid, tartronic acid, α-toluic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

The pharmaceutical compositions will typically be administered together with suitable carrier materials selected with respect to the intended form of administration, i.e. for oral administration in the form of tablets, capsules (either solid filled, semi-solid filled or liquid filled), and powders for constitution, aerosol preparations consistent with conventional pharmaceutical practices.

Other suitable formulations are gels, elixirs, dispersible granules, syrups, suspensions, creams, lotions, solutions, emulsions, suspensions, dispersions, and the like.

Suitable dosage forms for sustained release include tablets having layers of varying disintegration rates or controlled release polymeric matrices impregnated with the active components and shaped in tablet form or capsules containing such impregnated or encapsulated porous polymeric matrices. The pharmaceutical compositions may be comprised of 5 to 95% by weight of the peptides.

Lactose, starch, sucrose, cellulose, magnesium stearate, dicalcium phosphate, calcium sulfate, talc, mannitol, ethyl alcohol (liquid filled capsules) can be used as pharmaceutically acceptable carriers, excipients and/or diluents.

Suitable binders include starch, gelatin, natural sugars, corn sweeteners, natural and synthetic gums such as acacia, sodium alginate, carboxymethylcellulose, polyethylene glycol and waxes.

Among the lubricants that may be mentioned for use in these dosage forms, boric acid, sodium benzoate, sodium acetate, sodium chloride, and the like.

Disintegrants include starch, methylcellulose, guar gum and the like. Sweetening and flavoring agents and preservatives may also be included where appropriate.

Additionally, the compositions of the present invention may be formulated in sustained release form to provide the rate-controlled release of any one or more of the components or active ingredients to optimize the therapeutic effects.

Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

Also possible are solid form preparations, which are intended to be converted, shortly before use, to liquid form preparations for either oral or parenteral administration. Such liquid forms include solutions, suspensions and emulsions.

The peptides of the present invention may also be deliverable transdermally. The transdermal compositions may take the form of creams, lotions, aerosols and/or emulsions and can be included in a transdermal patch of the matrix or reservoir type as are conventional in the art for this purpose.

Powders for reconstitution refer to powder blends containing the active ingredients and suitable diluents, which can be suspended in water or juices. One example for such an oral administration form for newborns, toddlers and/or infants is a human breast milk substitute which is produced from milk powder and milk whey powder, optionally and partially substituted with lactose.

Suitable diluents are substances that usually make up the major portion of the composition or dosage form. Suitable diluents include sugars such as lactose, sucrose, mannitol and sorbitol, starches derived from wheat, corn rice and potato, and celluloses such as microcrystalline cellulose.

The amount of diluents in the composition can range from about 5 to about 95% by weight of the total composition, preferably from about 25 to about 75%, more preferably from about 30 to about 60% by weight, and most preferably from about 40 to 50% by weight.

The term disintegrants refers to materials added to the composition to help it break apart (disintegrate) and release the medicaments. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses and cross-linked microcrystalline celluloses such as sodium croscarmellose, alginates such as alginic acid and sodium alginate, clays such as bentonites, and effervescent mixtures.

The amount of disintegrant in the composition can range from about 1 to about 40% by weight of the composition, preferably 2 to about 30% by weight of the composition, more preferably from about 3 to 20% by weight of the composition, and most preferably from about 5 to about 10% by weight.

Binders characterize substances that bind or "glue" powders together and make them cohesive by forming granules, thus serving as the "adhesive" in the formulation. Binders add cohesive strength already available in the diluents or bulking agent. Suitable binders include sugars such as sucrose, starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropyl-methylcellulose; polyvinylpyrrolidone; and inorganics such as magnesium aluminum silicate.

The amount of binder in the composition can range from about 1 to 30% by weight of the composition, preferably from about 2 to about 20% by weight of the composition, more preferably from about 3 to about 10% by weight, even more preferably from about 3 to about 6% by weight.

Lubricant refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water-soluble lubricants such as sodium chloride, sodium benzoate, sodium acetate, sodium oleate, polyethylene glycols and d'l-leucine.

Lubricants are usually added at the very last step before compression, since they must be present on the surfaces of the granules and in between them and the parts of the tablet press.

The amount of lubricant in the composition can range from about 0.05 to about 15% by weight of the composition, preferably 0.2 to about 5% by weight of the composition, more preferably from about 0.3 to about 3%, and most preferably from about 0.3 to about 1.5% by weight of the composition.

Glidents are materials that prevent caking and improve the flow characteristics of granulations, so that flow is smooth and uniform. Suitable glidents include silicon dioxide and talc. The amount of glident in the composition can range from about 0.01 to about 10% by weight of the composition, preferably 0.1% to about 7% by weight of the total composition, more preferably from about 0.2 to 5% by weight, and most preferably from about 0.5 to about 2% by weight.

Coloring agents are excipients that provide coloration to the composition or the dosage form. Such excipients can include food grade dyes and food grade dyes adsorbed onto a suitable adsorbent such as clay or aluminum oxide. The amount of the coloring agent can vary from about 0.01 to 10% by weight of the composition, preferably from about 0.05 to 6% by weight, more preferably from about 0.1 to about 4% by weight of the composition, and most preferably from about 0.1 to about 1%.

The term buffer, buffer system, buffer solution and buffered solution, when used with reference to hydrogen-ion concentration or pH, refers to the ability of a system, particularly an aqueous solution, to resist a change of pH on adding acid or alkali, or on dilution with a solvent. Preferred buffer systems can be selected from the group consisting of formate (pKa=3.75), lactate (pKa=3.86), benzoic acid (pKa=4.2) oxalate (pKa=4.29), fumarate (pKa=4.38), aniline (pKa=4.63), acetate buffer (pKa=4.76), citrate buffer (pKa2=4.76, pKa3=6.4), glutamate buffer (pKa=4.3), phosphate buffer (pKa=7.20), succinate (pKa1=4.93; pKa2=5.62), pyridine (pKa=5.23), phthalate (pKa=5.41); histidine (pKa=6.04), MES (2-(N-morpholino)ethanesulphonic acid; pKa=6.15); maleic acid (pKa=6.26); cacodylate (dimethylarsinate, pKa=6.27), carbonic acid (pKa=6.35), ADA (N-(2-acetamido)imino-diacetic acid (pKa=6.62); PIPES (4-piperazinebis-(ethanesulfonic acid; BIS-TRIS-propane (1,3-bis[tris(hydroxymethyl)methyl-amino]-propane), pKa=6.80), ethylendiamine (pKa=6.85), ACES 2-[(2-amino-2-oxoethyl)amino]ethanesulphonic acid; pKa=6.9), imidazole (pKa=6.95), MOPS (3-(N-morphin)-propansulfonic acid; pKa=7.20), diethylmalonic acid (pKa=7.2), TES (2-[tris(hydroxymethyl)methyl]amino ethanesulfonic acid; pKa=7.50) and HEPES (N-2-hydroxylethylpiperazin-N'-2-ethansulfonic acid; pKa=7.55) buffers or other buffers having a pKa between 3.8 to 7.7.

Preferred is the group of carboxylic acid buffers such as acetate and carboxylic diacid buffers such as fumarate, tartrate and phthalate and carboxylic triacid buffers such as citrate. Inorganic buffers such as sulfate, borate, carbonate, oxalate, calcium hydroxyde and phosphate buffers represent another group of preferred buffers. Another group of preferred buffers are nitrogen-containing buffers such as imidazole, diethylenediamine, and piperazine.

Also preferred are sulfonic acid buffers such as TES, HEPES, ACES, PIPES, [(2-hydroxy-1,1-bis(hydroxymethyl)ethyl)amino]-1-propanesulfonic acid (TAPS), 4-(2-hydroxyethyl)piperazine-1-propanesulfonic acid (EPPS), 4-Morpholinepropanesulfonic acid (MOPS) and N,N-bis(2-hydroxyethyl)-2-aminoethanesulfonic acid (BES).

Another group of preferred buffers are glycine buffers such as glycine, glycyl-glycine, glycyl-glycyl-glycine, N,N-bis(2-hydroxyethyl)glycine and N-[2-hydroxy-1,1-bis(hydroxymethyl)ethyl]glycine (Tricine).

Preferred are also amino acid buffers such as glycine, alanine, valine, leucine, isoleucine, serine, threonine, phenylalanine, tyrosine, tryptophane, lysine, arginine, histidine, aspartate, glutamate, asparagine, glutamine, cysteine, methionine, proline, 4-hydroxyproline, N,N,N-trimethyllysine, 3-methylhistidine, 5-hydroxylysine, O-phosphoserine, γ-carboxyglutamate, ε-N-acetyllysine, ω-N-methylarginine, citrulline, ornithine and derivatives thereof.

Also preferred are the following buffers:

| effective pH range | pKa 25° C. | buffer |
| --- | --- | --- |
| 2.7-4.2 | 3.40 | malate (pK1) |
| 3.0-4.5 | 3.75 | formate |
| 3.0-6.2 | 4.76 | citrate (pK2) |
| 3.2-5.2 | 4.21 | succinate (pK1) |
| 3.6-5.6 | 4.76 | acetate |
| 3.8-5.6 | 4.87 | propionate |
| 4.0-6.0 | 5.13 | malate (pK2) |
| 4.9-5.9 | 5.23 | pyridine |
| 5.0-6.0 | 5.33 | piperazine (pK1) |
| 5.0-7.4 | 6.27 | cacodylate |
| 5.5-6.5 | 5.64 | succinate (pK2) |
| 5.5-6.7 | 6.10 | MES |
| 5.5-7.2 | 6.40 | citrate (pK3) |
| 5.5-7.2 | 6.24 | maleate (pK2) |
| 5.5-7.4 | 1.70, 6.04, 9.09 | histidine |
| 5.8-7.2 | 6.46 | bis-tris |
| 5.8-8.0 | 7.20 | phosphate (pK2) |
| 6.0-12.0 | 9.50 | ethanolamine |
| 6.0-7.2 | 6.59 | ADA |
| 6.0-8.0 | 6.35 | carbonate (pK1) |
| 6.1-7.5 | 6.78 | ACES |
| 6.1-7.5 | 6.76 | PIPES |
| 6.2-7.6 | 6.87 | MOPSO |
| 6.2-7.8 | 6.95 | imidazole |
| 6.3-9.5 | 6.80, 9.00 | BIS-TRIS propane |
| 6.4-7.8 | 7.09 | BES |

| effective pH range | pKa 25° C. | buffer |
| --- | --- | --- |
| 6.5-7.9 | 7.14 | MOPS |
| 6.8-8.2 | 7.48 | HEPES |
| 6.8-8.2 | 7.40 | TES |
| 6.9-8.3 | 7.60 | MOBS |
| 7.0-8.2 | 7.52 | DIPSO |
| 7.0-8.2 | 7.61 | TAPSO |
| 7.0-8.3 | 7.76 | triethanolamine (TEA) |
| 7.0-9.0 | 0.91, 2.10, 6.70, 9.32 | pyrophosphate |
| 7.1-8.5 | 7.85 | HEPPSO |
| 7.2-8.5 | 7.78 | POPSO |

Preferred are the buffers having an effective pH range of from 2.7 to 8.5, and more preferred of from 3.8 to 7.7. The effective pH range for each buffer can be defined as pKa−1 to pKa+1, where Ka is the ionization constant for the weak acid in the buffer and pKa=−log K.

Most preferred are buffers suitable for pharmaceutical use e.g. buffers suitable for administration to a patient such as acetate, carbonate, citrate, fumarate, glutamate, lactate, phosphate, phthalate, and succinate buffers. Particularly preferred examples of commonly used pharmaceutical buffers are acetate buffer, citrate buffer, glutamate buffer and phosphate buffer. Also most preferred is the group of carboxylic acid buffers.

The term "carboxylic acid buffers" as used herein shall refer to carboxylic monoacid buffers and carboxylic diacid buffers as well as carboxylic triacid buffers. Of course also combinations of buffers, especially of the buffers mentioned herein are useful.

Some suitable pharmaceutical buffers are a citrate buffer (preferably at a final formulation concentration of from about 20 to 200 mM, more preferably at a final concentration of from about 30 to 120 mM) or an acetate buffer (preferably at a final formulation concentration of about 20 to 200 mM) or a phosphate buffer (preferably at a final formulation concentration of about 20 to 200 mM).

Techniques for the formulation and administration of the peptides are well known to a skilled person. A suitable composition comprising at least one peptide mentioned herein may be a solution of the peptide in a suitable liquid pharmaceutical carrier or any other formulation such as tablets, pills, film tablets, coated tablets, dragees, capsules, powders and deposits, gels, syrups, slurries, suspensions, emulsions, and the like.

A particularly preferred pharmaceutical composition is a lyophilised (freeze-dried) preparation suitable for administration by inhalation or for intravenous administration. To prepare the preferred lyophilised preparation the peptide of the invention is solubilised in a 4 to 5% (w/v) mannitol solution and the solution is then lyophilised. The mannitol solution can also be prepared in a suitable buffer solution as described above.

Further examples of suitable cryo-/lyoprotectants (otherwise referred to as bulking agents or stabilizers) include thiol-free albumin, immunoglobulins, polyalkyleneoxides (e.g. PEG, polypropylene glycols), trehalose, glucose, sucrose, sorbitol, dextran, maltose, raffinose, stachyose and other saccharides, while mannitol is used preferably. These can be used in conventional amounts in conventional lyophilization techniques. Methods of lyophilisation are well known in the art of preparing pharmaceutical formulations.

For administration by inhalation the particle diameter of the lyophilised preparation is preferably 1 to 10 μm, more preferably between 2 to 5 μm, most preferably between 3 to 4 μm. The lyophilised preparation is particularly suitable for administration using an inhalator, for example the VENTA-NEB® inhalator (NEBU-TEC, Elsenfeld, Germany). The lyophilised product can be rehydrated in sterile distilled water or any other suitable liquid for inhalation administration.

Alternatively for injectable administration the lyophilised product can be rehydrated in sterile distilled water or any other suitable liquid for injectable administration.

After rehydration for administration in sterile distilled water or another suitable liquid the lyophilised preparation should have the approximate physiological osmolality of the target tissue for the rehydrated peptide preparation i.e. blood for intravenous administration or lung tissue for inhalation administration. Thus it is preferred that the rehydrated formulation is substantially isotonic.

Treatment

The term "treatment" in the context of the present invention refers to the use of the peptides to inhibit, or arrest the symptoms of infection, in particular viral, bacterial, fungal, protozoan infection, and/or a disease caused by microorganisms, such as viruses, bacteria, fungi, or protozoans. In some instances, treatment with the peptides can be done in combination with other protective compounds to inhibit, or arrest the symptoms of bacteria infection and/or a disease caused by microorganisms, such as bacteria, fungi, or protozoans.

The term "active agent" or "therapeutic agent" as used herein refers to an agent that can prevent, inhibit, or arrest the symptoms and/or progression of an infectious disease.

The term "therapeutic effect" as used herein, refers to the effective provision of protection effects to prevent, inhibit, or arrest the symptoms and/or progression of a disease caused by microorganisms, such as bacteria, fungi, or protozoans.

The term "a therapeutically effective amount" as used herein means a sufficient amount of the peptides of the invention to produce a therapeutic effect, as defined above, in a subject or patient in need of treatment.

The terms "subject" or "patient" are used herein mean any mammal, including but not limited to human beings, including a human patient or subject to which the compositions of the invention can be administered. The term mammals include human patients and non-human primates, as well as experimental animals such as rabbits, rats, and mice, and other animals.

In one aspect, the present invention relates to a method for the treatment of a disease, disorder or condition caused by, associated with or accompanied by an infection, preferably a viral, bacterial, fungal, and/or protozoan infection, more preferably a bacterial and/or fungal infection, comprising administering a pharmaceutically effective amount of a composition according to the invention or pharmaceutical composition according to the invention to a subject in need thereof.

In a preferred embodiment, the bacterial infection is caused by Gram-negative bacteria, in particular by *Pseudomonas aeruginosa*, *Escherichia coli*, and/or *Salmonella*, Gram-positive bacteria, in particular by *Staphylococcus aureus, Staphylococcus epidermidis*, and/or *Enterococcus faecalis*, and/or by *Mycobacterium tuberculosis*.

In a further preferred embodiment, the fungal infection is caused by pathogenic yeast species, in particular by *Candida albicans*.

In a further preferred embodiment the composition according to the invention or pharmaceutical composition according to the invention is used for prophylaxis and/or treatment of bacterial infection and/or a disease caused by microorganisms, such as bacteria, fungi, or protozoans, in birds.

In a more preferred embodiment the composition according to the invention or pharmaceutical composition according to the invention is used for prophylaxis and/or treatment of bacteria infection and/or a disease caused by microorganisms, such as bacteria, fungi, or protozoans, in birds of prey. The group of birds of prey comprises but is not restricted to eagles, falcons, hawks and owls.

In a most preferred embodiment falcons are treated with the peptides. Falcons can be treated virtually with the same medicamentation and equipment as e.g. humans. It is within the scope of the skilled artisan to adjust e.g. the concentration and dosage form in suitable ways.

Definition of Peptide Activity

The peptides are deemed to have therapeutic activity if they demonstrated to inhibit the growth of microorganisms or are able to kill the microorganisms. As used herein, the term "peptide" shall also refer to salts, hydrates, and acylated forms of the peptides mentioned herein. Suitable protecting groups for amino groups are the benzyloxycarbonyl, t-butyloxycarbonyl (BOC), formyl, and acetyl or acyl group. Suitable protecting groups for the carboxylic acid group are esters such as benzyl esters or t-butyl esters.

EXAMPLES

Example 1

```
WKWLKKWIK           SEQ ID NO 1

WRKFWKYLK           SEQ ID NO 2

RRWRVIVKW           SEQ ID NO 3
```

The peptides are synthesized using standard Fmoc-strategy on cellulose with the SPOT technology; they are positively charged peptides, which were then cleaved from the cellulose and solubilized in water. Peptides were transferred into wells containing luminescent bacteria, in 0.1 M Tris buffer (pH 7.4), containing 20 mM glucose. After 4 hours of incubation time, the luminescence was measured using a microtiter plate reader. Consequently, 50 µl of Mueller-Hinton media was added in order to check for recovery of the bacteria. The plates were manually inspected after 18 h of incubation time. In addition, the following peptides were synthesized, tested, and showed antimicrobial activity: WKWRVRVTI (SEQ ID NO.:27), YRLRVKWKW (SEQ ID NO.:26), RIRRWKFRW (SEQ ID NO.:6), RQRRWIWW (SEQ ID NO.:24), KRRWRIWLV (SEQ ID NO.:15), RTKKWIVWI (SEQ ID NO.:28), LRRWIRIRW (SEQ ID NO.:21), RLKRWWKFL (SEQ ID NO.:7), KFKWWRMLI (SEQ ID NO.:10), KRKKRFKWW (SEQ ID NO.:29), RRRWWKLMM (SEQ ID NO.:20), RKFRWWVIR (SEQ ID NO.:22).

Example 2

A broth dilution method, which is one of the most commonly used technique to determine the Minimal Inhibitory Concentration (MIC; The lowest concentration that is able to inhibit growth of the microorganisms) of antimicrobial agents was used. The protocol was adjusted for the peptides and is based on the guidelines of the two established organizations and committees, the CLSI (Clinical and Laboratory Standards Institute) and EUCAST (European Committee for Antimicrobial Susceptibility Testing). Briefly, The MIC of the peptides was measured in Mueller Hinton (MH) medium, whereby the assay was performed in sterile 96-well round bottom polypropylene microtiter plates with an inoculum of $2-7\times10^5$ colony forming units (CFU) per ml. The plates were incubated at 37° C. for 12-15 h and the MIC was reported as the minimal peptide concentration at which no growth is observed.

Example 3

Inhibition of *Escherichia coli* (Gram-Negative Bacteria)

Minimal inhibitory concentration (MIC) values were determined and are reported as µmol $I^{-1}$. The bacterial strain used for the MIC determination assay was *Escherichia coli* (*E. coli*) UB1005 (F—, nalA37, metB1).

Results:

| Sequence | MIC |
| --- | --- |
| WKWLKKWIK (SEQ ID NO.:1) | 5.8 |
| WRKFWKYLK (SEQ ID NO.:2) | 0.8 |
| RRWRVIVKW (SEQ ID NO.:3) | 1.3 |

Peptides of the invention are inhibitors of *Escherichia coli* growth and replication and useful for the preparation of medicaments to treat *Escherichia coli* caused diseases.

Example 4

Inhibition of *Salmonella* (Gram-Negative Bacteria)

Minimal inhibitory concentration (MIC) values were determined and are reported as µmol $I^{-1}$. The bacterial strain used for the MIC determination assay was the wild-type *Salmonella enterica* ssp. *Typhimurium* (*S. typhimurium*) strain.

Results:

| Sequence | MIC |
| --- | --- |
| WKWLKKWIK (SEQ ID NO.:1) | 11.5 |
| WRKFWKYLK (SEQ ID NO.:2) | 6.0 |
| RRWRVIVKW (SEQ ID NO.:3) | 2.7 |

Peptides of the invention are inhibitor of *Salmonella* growth and replication and useful for the preparation of medicaments to treat *Salmonella* caused diseases.

Example 5

Inhibition of *Pseudomonas aeruginosa* (Gram-Negative Bacteria)

Minimal inhibitory concentration (MIC) values were determined and are reported as µmol $I^{-1}$. The bacterial strain used for the MIC determination assay was the *Pseudomonas aeruginosa* (*P. aeruginosa*) H103 strain.

Results:

| Sequence | MIC |
| --- | --- |
| WKWLKKWIK (SEQ ID NO.:1) | 2.9 |
| WRKFWKYLK (SEQ ID NO.:2) | 6.0 |
| RRWRVIVKW (SEQ ID NO.:3) | 2.7 |

Peptides of the invention are inhibitors of *Pseudomonas aeruginosa* growth and replication and useful for the preparation of medicaments to treat *Pseudomonas aeruginosa* caused diseases.

Example 6

Inhibition of Multi-Drug Resistant *Pseudomonas aeruginosa* (Gram-Negative Bacteria)

Minimal inhibitory concentration (MIC) values were determined and are reported as µmol $l^{-1}$. The bacterial strain used for the MIC determination assay was a clinical multi-drug resistant *Pseudomonas aeruginosa* strain.
Result:

| Sequence | MIC |
| --- | --- |
| RRWRVIVKW (SEQ ID NO.:3) | 2.7 |

Peptide of the invention is an inhibitor of multi-drug resistant *Pseudomonas aeruginosa* growth and replication and useful for the preparation of medicaments to treat multi-drug resistant *Pseudomonas aeruginosa* caused diseases.

Example 7

Inhibition of *Enterococcus faecalis* (Gram-Positive Bacteria)

Minimal inhibitory concentration (MIC) values were determined and are reported as µmol $l^{-1}$. The bacterial strain used for the MIC determination assay was the *Enterococcus faecalis* (*E. faecalis*) ATCC29212 strain.
Results:

| Sequence | MIC |
| --- | --- |
| WKWLKKWIK (SEQ ID NO.:1) | 11.5 |
| WRKFWKYLK (SEQ ID NO.:2) | 6.0 |
| RRWRVIVKW (SEQ ID NO.:3) | 2.7 |

Peptides of the invention are inhibitors of *Enterococcus faecalis* growth and replication and useful for the preparation of medicaments to treat *Enterococcus faecalis* caused diseases.

Example 8

Inhibition of *Staphylococcus aureus* (Gram-Positive Bacteria)

Minimal inhibitory concentration (MIC) values were determined and are reported as µmol $l^{-1}$. The bacterial strain used for the MIC determination assay was the *Staphylococcus aureus* (*S. aureus*) ATCC25923 strain.
Results:

| Sequence | MIC |
| --- | --- |
| WKWLKKWIK (SEQ ID NO.:1) | 0.7 |
| WRKFWKYLK (SEQ ID NO.:2) | 0.8 |
| RRWRVIVKW (SEQ ID NO.:3) | 1.3 |

Peptides of the invention are inhibitors of *Staphylococcus aureus* growth and replication and useful for the preparation of medicaments to treat *Staphylococcus aureus* caused diseases.

Example 9

Inhibition of *Staphylococcus epidermidis* (Gram-Positive Bacteria)

Minimal inhibitory concentration (MIC) values were determined and are reported as µmol $l^{-1}$. The bacterial strain used for the MIC determination assay was a *Staphylococcus epidermidis* clinical strain.
Results:

| Sequence | MIC |
| --- | --- |
| WKWLKKWIK (SEQ ID NO.:1) | 0.7 |
| WRKFWKYLK (SEQ ID NO.:2) | 0.8 |
| RRWRVIVKW (SEQ ID NO.:3) | 0.7 |

Peptides of the invention are inhibitors of *Staphylococcus epidermidis* growth and replication and useful for the preparation of medicaments to treat *Staphylococcus epidermidis* caused diseases.

Example 10

Inhibition of *Mycobacterium tuberculosis*

Minimal inhibitory concentration (MIC) values were determined and are reported as µmol $l^{-1}$. The bacterial strain used for the MIC determination assay was the *Mycobacterium tuberculosis* H37Rv strain.
Results:

| Sequence | MIC |
| --- | --- |
| WKWLKKWIK (SEQ ID NO.:1) | 1.1 |
| WRKFWKYLK (SEQ ID NO.:2) | 3.0 |

Peptides of the invention are inhibitors of *Mycobacterium tuberculosis* growth and replication and useful for the preparation of medicaments to treat *Mycobacterium tuberculosis* caused diseases.

Example 11

Inhibition of *Candida albicans* (Yeast)

Antifungal activity was tested using a laboratory isolate of *Candida albicans*.

Minimal inhibitory concentration (MIC) values were determined and are reported as µmol I$^{-1}$.

Results:

| Sequence | MIC |
|---|---|
| WKWLKKWIK (SEQ ID NO.:1) | 5.8 |
| WRKFWKYLK (SEQ ID NO.:2) | 3.0 |
| RRWRVIVKW (SEQ ID NO.:3) | 5.4 |

Peptides of the invention are inhibitors of *Candida albicans* growth and replication and useful for the preparation of medicaments to treat *Candida albicans* caused diseases.

Example 12

Hemolytic Activity Assessment

Human blood was used to test the peptide for hemolytic effects. The toxic effect was assessed by hemoglobin release from human red blood cells resulting from cell lysis, according to standard procedures, modified to be carried out in 96-well polypropylene microtiter plates for high-throughput screening. Briefly, the blood was washed with PBS, diluted with PBS and transferred into 96 well plates. Peptides were added as a premade dilution series and incubated at 37° C. for 1 hour. Triton X was used for the 100% hemolysis value. Hemoglobin release was monitored chromogenically at 414 and 546 nm using and ELISA plate reader. HC$_{50}$ values (the mean concentration of peptides producing 50% hemolysis of human blood) are reported as µmol I$^{-1}$.

Results:

| Sequence | HC$_{50}$ |
|---|---|
| WKWLKKWIK (SEQ ID NO.:1) | 80 |
| WRKFWKYLK (SEQ ID NO.:2) | >128 |
| RRWRVIVKW (SEQ ID NO.:3) | 54 |

Peptides of the invention are not toxic to human cells and useful for the preparation of medicament to treat infectious diseases.

The invention claimed is:

1. A composition comprising a combination of the nonapeptides having the sequences WKWLKKWIK (SEQ ID NO.:1), WRKFWKYLK (SEQ ID NO.:2), and RRWRVIVKW (SEQ ID NO.:3).

2. The composition according to claim 1 for use in medicine.

3. The composition according to claim 1, for use in the treatment of infections caused by bacteria and fungi.

4. The composition according to claim 1, for use in the treatment of bacterial infections or diseases caused by bacteria.

5. The composition for use according to claim 4, wherein the bacterial infection or disease is caused by infection with Gram-negative bacteria.

6. The composition for use according to claim 4, wherein the bacterial infection or disease is caused by infection with Gram-positive bacteria.

7. The composition for use according to claim 4, wherein the bacterial infection or disease is caused by infection with *Mycobacterium tuberculosis*.

8. The composition according to claim 1, for use in the treatment of fungal infections or diseases caused by fungi.

9. The composition for use according to claim 8, wherein the fungal infection or disease is caused by infection with pathogenic yeast species.

10. Pharmaceutical composition comprising a composition according to claim 1 and at least one pharmaceutically acceptable carrier, cryoprotectant, lyoprotectant, excipient and/or diluent.

11. Pharmaceutical composition according to claim 10 in the form of an artificial mother milk formulation or mother milk substitute suitable for oral delivery to newborns, toddlers and infants.

12. Pharmaceutical composition according to claim 10 in the form of a formulation for coating medical implants.

13. A composition comprising a nonapeptide having the sequence WKWLKKWIK (SEQ ID NO.:1).

14. A composition comprising a nonapeptide having the sequence WRKFWKYLK (SEQ ID NO.:2).

15. A composition comprising a nonapeptide having the sequence RRWRVIVKW (SEQ ID NO.:3).

16. The composition according to claim 13 for use in medicine.

17. The composition according to claim 13, for use in the treatment of infections caused by bacteria and/or fungi.

18. The composition according to claim 13, for use in the treatment of bacterial infections or diseases caused by bacteria.

19. The composition for use according to claim 18, wherein the bacterial infection or disease is caused by infection with Gram-negative bacteria.

20. The composition for use according to claim 18, wherein the bacterial infection or disease is caused by infection with Gram-positive bacteria.

21. The composition for use according to claim 18, wherein the bacterial infection or disease is caused by infection with *Mycobacterium tuberculosis*.

22. The composition according to claim 13, for use in the treatment of fungal infections or diseases caused by fungi.

23. The composition for use according to claim 22, wherein the fungal infection or disease is caused by infection with pathogenic yeast species.

24. Pharmaceutical composition comprising a composition according to claim 13 and at least one pharmaceutically acceptable carrier, cryoprotectant, lyoprotectant, excipient and/or diluent.

25. Pharmaceutical composition according to claim 24 in the form of an artificial mother milk formulation or mother milk substitute suitable for oral delivery to newborns, toddlers and infants.

26. Pharmaceutical composition according to claim 24 in the form of a formulation for coating medical implants.

27. A method for the treatment of a disease, disorder or condition caused by, or accompanied by bacterial and/or fungal infection, comprising administering a pharmaceutically effective amount of a composition according to claim 1 to a subject in need thereof.

28. The method according to claim 27, wherein the bacterial infection is caused by Gram-negative bacteria or Gram-positive bacteria.

29. The method according to claim 27, wherein the fungal infection is caused by pathogenic yeast species.

30. The method according to claim 27, wherein the subject in need thereof is a mammal or a bird.

31. The composition for use according to claim 9, wherein the pathogenic yeast species is *Candida albicans*.

32. The composition for use according to claim 23, wherein the pathogenic yeast species is *Candida albicans*.

33. The method according to claim 29, wherein the pathogenic yeast species is *Candida albicans*.

34. The method according to claim 30, wherein the mammal is a human, or the bird is a bird of prey.

35. The composition for use according to claim 6, wherein the Gram-positive bacteria is selected from the group consisting of *Staphylococcus aureus, Staphylococcus epidermidis*, and *Enterococcus faecalis*.

36. The composition for use according to claim 20, wherein the Gram-positive bacteria is selected from the group consisting of *Staphylococcus aureus, Staphylococcus epidermidis*, and *Enterococcus faecalis*.

37. The method according to claim 28, wherein the Gram-negative bacteria is selected from the group consisting of *Pseudomonas aeruginosa, Escherichia coli*, and *Salmonella*, or the Gram-positive bacteria is selected from the group consisting of *Staphylococcus aureus, Staphylococcus epidermidis, Enterococcus faecalis*, and *Mycobacterium tuberculosis*.

38. The composition for use according to claim 5, wherein the Gram-negative bacteria is selected from the group consisting of *Pseudomonas aeruginosa, Escherichia coli*, and *Salmonella*.

39. The composition for use according to claim 19, wherein the Gram-negative bacteria is selected from the group consisting of *Pseudomonas aeruginosa, Escherichia coli*, and *Salmonella*.

* * * * *